(12) United States Patent
Trawick

(10) Patent No.: US 9,993,240 B2
(45) Date of Patent: Jun. 12, 2018

(54) MENISCAL REPAIR DEVICE

(71) Applicant: Roy H. Trawick, Murray, UT (US)

(72) Inventor: Roy H. Trawick, Murray, UT (US)

( * ) Notice: Subject to any disclaimer, the term of this patent is extended or adjusted under 35 U.S.C. 154(b) by 935 days.

(21) Appl. No.: 14/179,413

(22) Filed: Feb. 12, 2014

(65) Prior Publication Data

US 2015/0223803 A1 Aug. 13, 2015

(51) Int. Cl.
*A61B 17/04* (2006.01)

(52) U.S. Cl.
CPC .. *A61B 17/0401* (2013.01); *A61B 2017/0409* (2013.01); *A61B 2017/0417* (2013.01); *A61B 2017/0464* (2013.01)

(58) Field of Classification Search
CPC ........ A61B 17/0401; A61B 2017/0409; A61B 2017/0417; A61B 17/0057
See application file for complete search history.

(56) References Cited

U.S. PATENT DOCUMENTS

| | | | |
|---|---|---|---|
| 5,531,759 A * | 7/1996 | Kensey | A61B 17/0401 604/15 |
| 5,662,681 A * | 9/1997 | Nash | A61B 17/0057 604/285 |
| 5,928,252 A | 7/1999 | Steadman et al. | |
| 7,594,922 B1 | 9/2009 | Goble et al. | |
| 8,088,130 B2 | 1/2012 | Kaiser et al. | |
| 8,177,795 B2 | 5/2012 | Niese et al. | |
| 8,409,253 B2 | 4/2013 | Stone et al. | |
| 8,449,533 B2 | 5/2013 | Saliman et al. | |
| 8,500,809 B2 | 8/2013 | Saliman | |
| 8,512,374 B2 | 8/2013 | Schwartz et al. | |
| 8,551,140 B2 | 10/2013 | Denham et al. | |
| 8,562,631 B2 | 10/2013 | Saliman et al. | |
| 8,562,647 B2 | 10/2013 | Kaiser et al. | |
| 8,574,235 B2 | 11/2013 | Stone | |
| 8,652,172 B2 | 2/2014 | Denham et al. | |
| 2004/0015186 A1 | 1/2004 | Bittar | |

(Continued)

FOREIGN PATENT DOCUMENTS

| | | |
|---|---|---|
| CA | 2698802 | 10/2010 |
| EP | 2098172 | 9/2009 |

(Continued)

OTHER PUBLICATIONS

Arthrex, Inc., "Comprehensive Solutions to Arthroscopic Meniscal Repair," 2010.

(Continued)

*Primary Examiner* — Gregory Anderson
(74) *Attorney, Agent, or Firm* — Morriss O'Bryant Compagni Cannon, PLLC

(57) ABSTRACT

An implant for repairing tears in soft tissue, such as a meniscus, may include a lead anchoring member and a trailing anchoring member interlaced by a looped strand member. The lead anchoring member and the trailing anchoring member may be formed of a suture material having a diameter greater than a diameter of the strand member. The lead anchoring member and the trailing anchoring member may deform into a suture mass in response to a lead of the strand member being placed under tension to thereby cinch the looped portion. A self-locking locking knot may prevent loosening of the looped portion.

48 Claims, 10 Drawing Sheets

(56) References Cited

U.S. PATENT DOCUMENTS

| | | |
|---|---|---|
| 2005/0125031 A1* | 6/2005 | Pipenhagen ....... A61B 17/0057 606/213 |
| 2006/0280768 A1 | 12/2006 | Hwang et al. |
| 2007/0010857 A1 | 1/2007 | Sugimoto et al. |
| 2007/0010875 A1 | 1/2007 | Sugimoto et al. |
| 2009/0082806 A1 | 3/2009 | West, Jr. et al. |
| 2010/0010497 A1 | 1/2010 | Goble et al. |
| 2010/0249809 A1 | 9/2010 | Singhatat et al. |
| 2010/0305583 A1 | 12/2010 | Baird et al. |
| 2011/0022083 A1 | 1/2011 | DiMatteo et al. |
| 2011/0022084 A1 | 1/2011 | Sengun et al. |
| 2011/0112556 A1 | 5/2011 | Saliman et al. |
| 2011/0218557 A1 | 9/2011 | Saliman |
| 2011/0270278 A1 | 11/2011 | Overes et al. |
| 2012/0239062 A1 | 9/2012 | Saliman |
| 2012/0265221 A1 | 10/2012 | Saliman et al. |
| 2012/0283750 A1 | 11/2012 | Saliman et al. |
| 2013/0123844 A1* | 5/2013 | White ................ A61B 17/0057 606/232 |
| 2013/0138123 A1 | 5/2013 | Stone et al. |
| 2013/0190813 A1* | 7/2013 | Tegels ................ A61B 17/0057 606/214 |
| 2013/0238040 A1 | 9/2013 | Saliman et al. |
| 2013/0282060 A1 | 10/2013 | Tuval |

FOREIGN PATENT DOCUMENTS

| | | |
|---|---|---|
| EP | 2455003 | 8/2012 |
| WO | 2009/042468 | 4/2009 |

OTHER PUBLICATIONS

Biomet, Inc., "MaxFire™ MarXmen™ Meniscal Repair Device with ZipLoop™ Technology," 2013.

Greaves et al., "The Biomechanical Performance of the Fast-Fix 360 Meniscal Repair System," Smith & Nephew Fast-Fix 360 Meniscal Repair System, 2010.

* cited by examiner

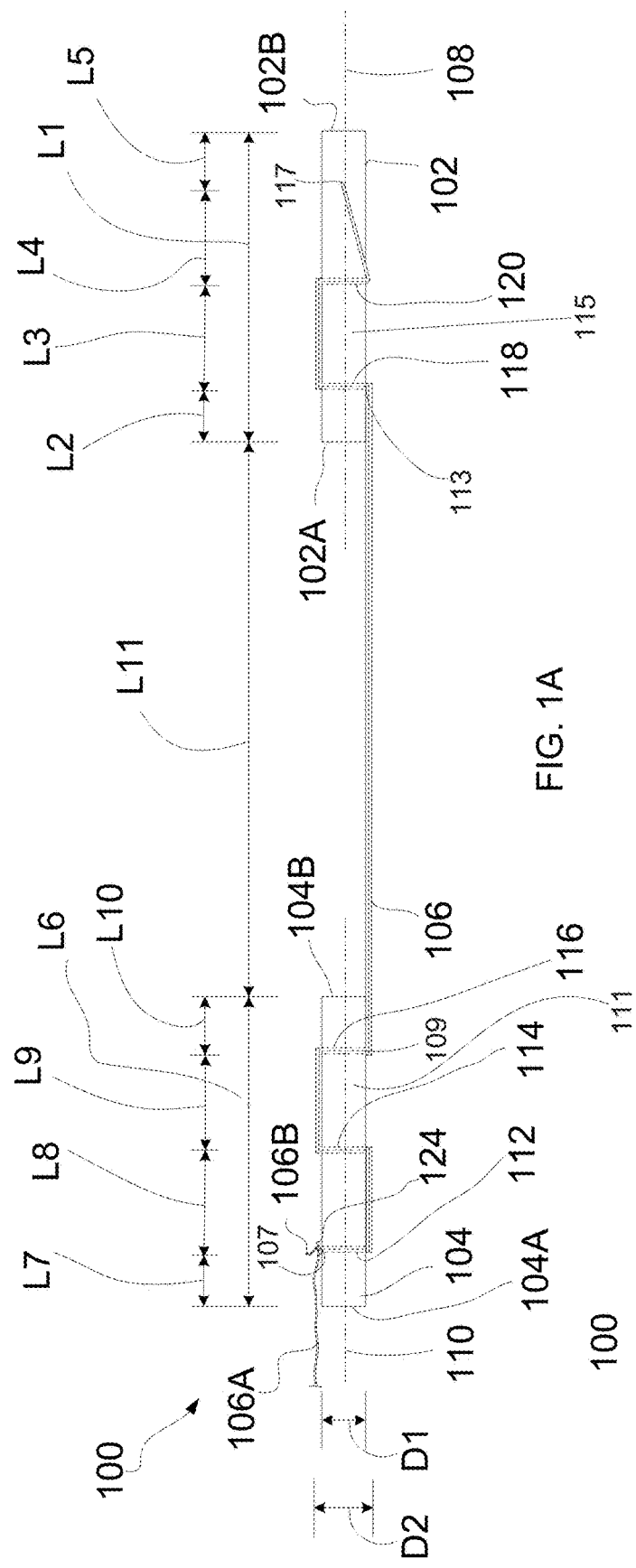
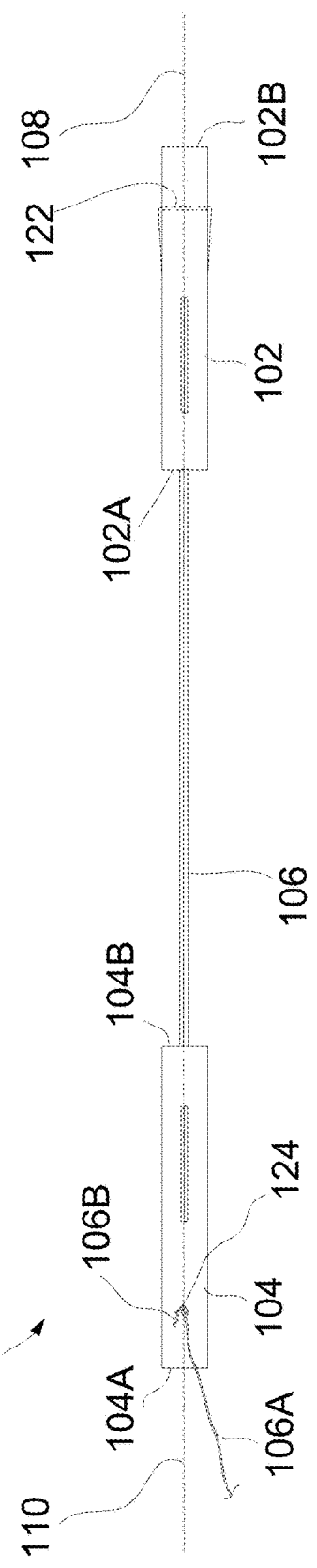
FIG. 1A
FIG. 1B

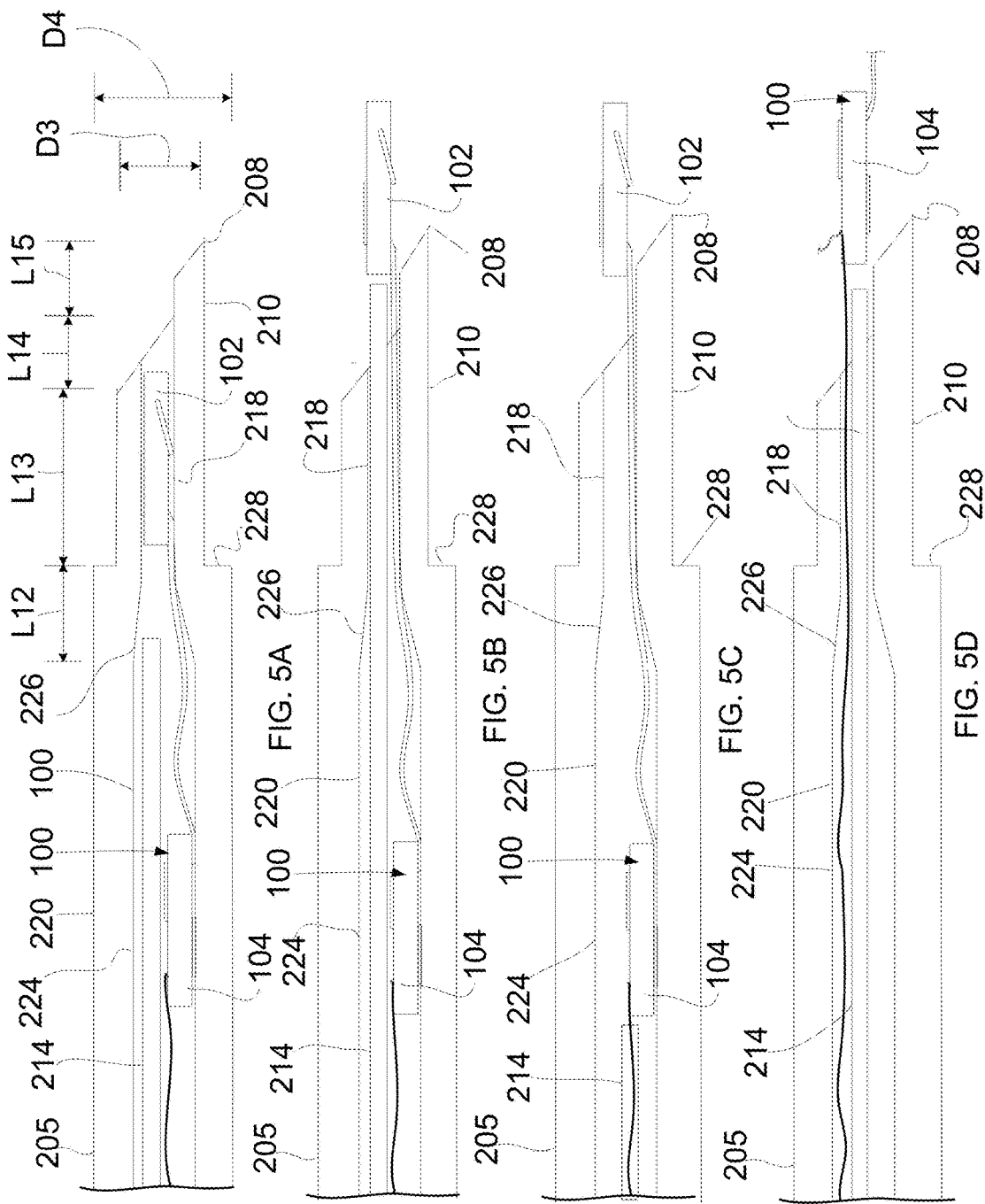

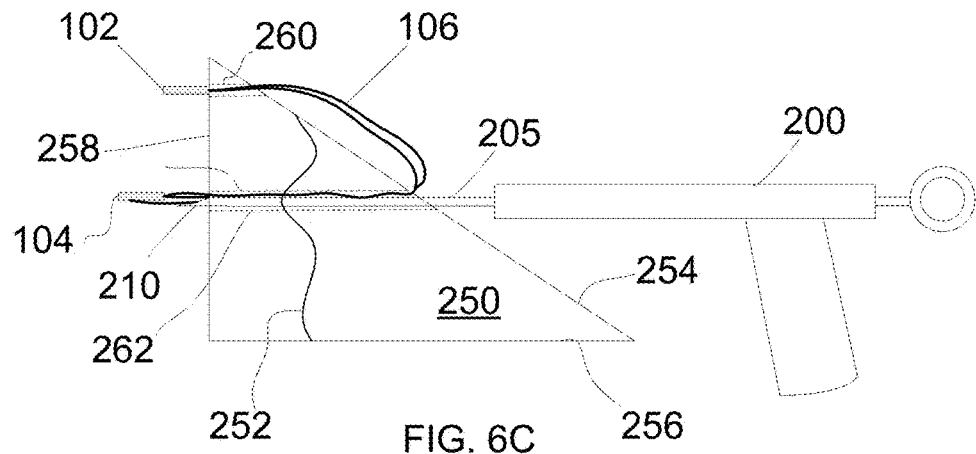
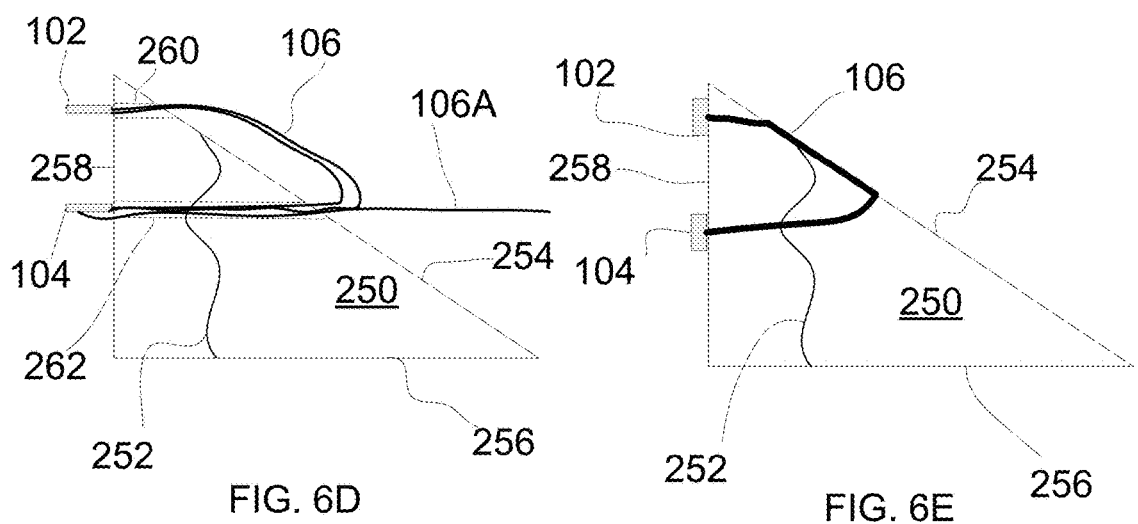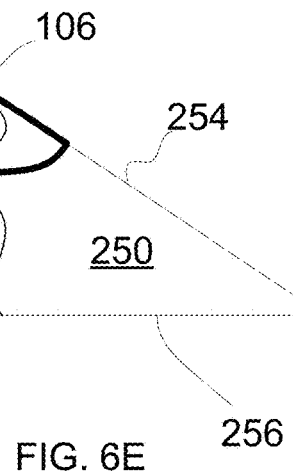
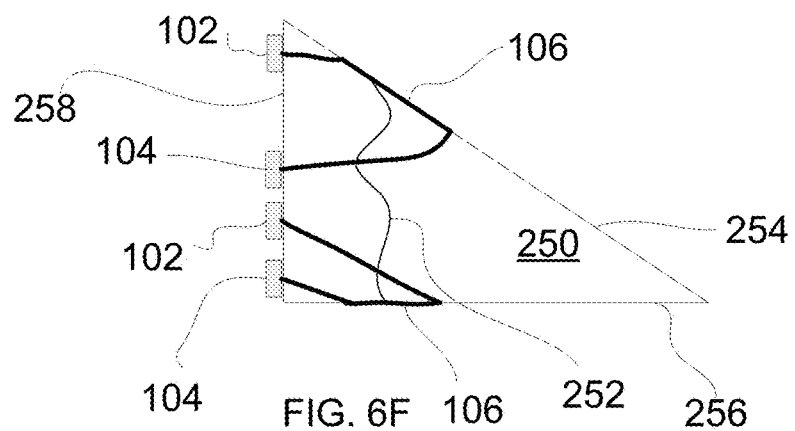

MENISCAL REPAIR DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

1. The Field of the Present Disclosure

The present disclosure relates generally to medical implants, and more particularly, but not necessarily entirely, to medical implants for repairing injuries, such as tears, to soft tissue.

2. Description of Related Art

Soft tissue tears are a common injury to the cartilage that stabilizes and cushions the joints. The meniscus, a crescent-shaped fibrocartilaginous structure in the knee joint, is particularly susceptible to injury due today's active lifestyles of many individuals. Small tears to the meniscus may heal on their own. Moderate to large tears in the meniscus may require surgical repair. Various techniques have been developed by surgeons for repairing tears in the meniscus, including inside-out techniques and all-inside techniques, as explained below.

The inside-out technique for meniscal repair may be considered the gold standard means of meniscal repair. Multiple studies have demonstrated its efficacy and superior biomechanical strength. However, given its longer surgical time and complexity, as well as the advent of multiple all-inside repair devices and techniques, the inside-out repair is used far less frequently today than in the past. From a patient standpoint, however, this evolution may not represent progress. Only vertical mattress stitches placed on both the superior and inferior surfaces of a meniscal tear may result in anatomic reduction of a tear with 100% tissue apposition. Techniques and device developed for all-inside repairs may be deployed only on the superior surface of the tear, and as the sutures are tightened down, the meniscus may pucker, with tissue apposition superiorly, and gapping inferiorly. Further, most all-inside devices cut a sizeable channel through the meniscus tissue with their beveled cutting-tip delivery instruments. A return to the principles of inside-out repair, with superior and inferior surface stitches, as well as anatomic reduction of the tear, may have an immediate and significant impact on patient recovery time and satisfaction.

The prior art is thus characterized by several disadvantages that are addressed by the present disclosure. The present disclosure minimizes, and in some aspects eliminates, the above-mentioned failures, and other problems, by utilizing the methods and structural features described herein. The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 1A is a side view of an implant for soft tissue repair according to an embodiment of the present disclosure;

FIG. 1B is a top view of the implant shown in FIG. 1 according to an embodiment of the present disclosure;

FIGS. 5A-5D depict an insertion procedure of the implant shown in FIG. 1 using the implant inserter shown in FIG. 4;

FIGS. 6A-6F depict an insertion procedure of multiple implants shown in FIG. 1 using the implant inserter shown in FIG. 4 into soft tissue;

DETAILED DESCRIPTION

Figure 2:
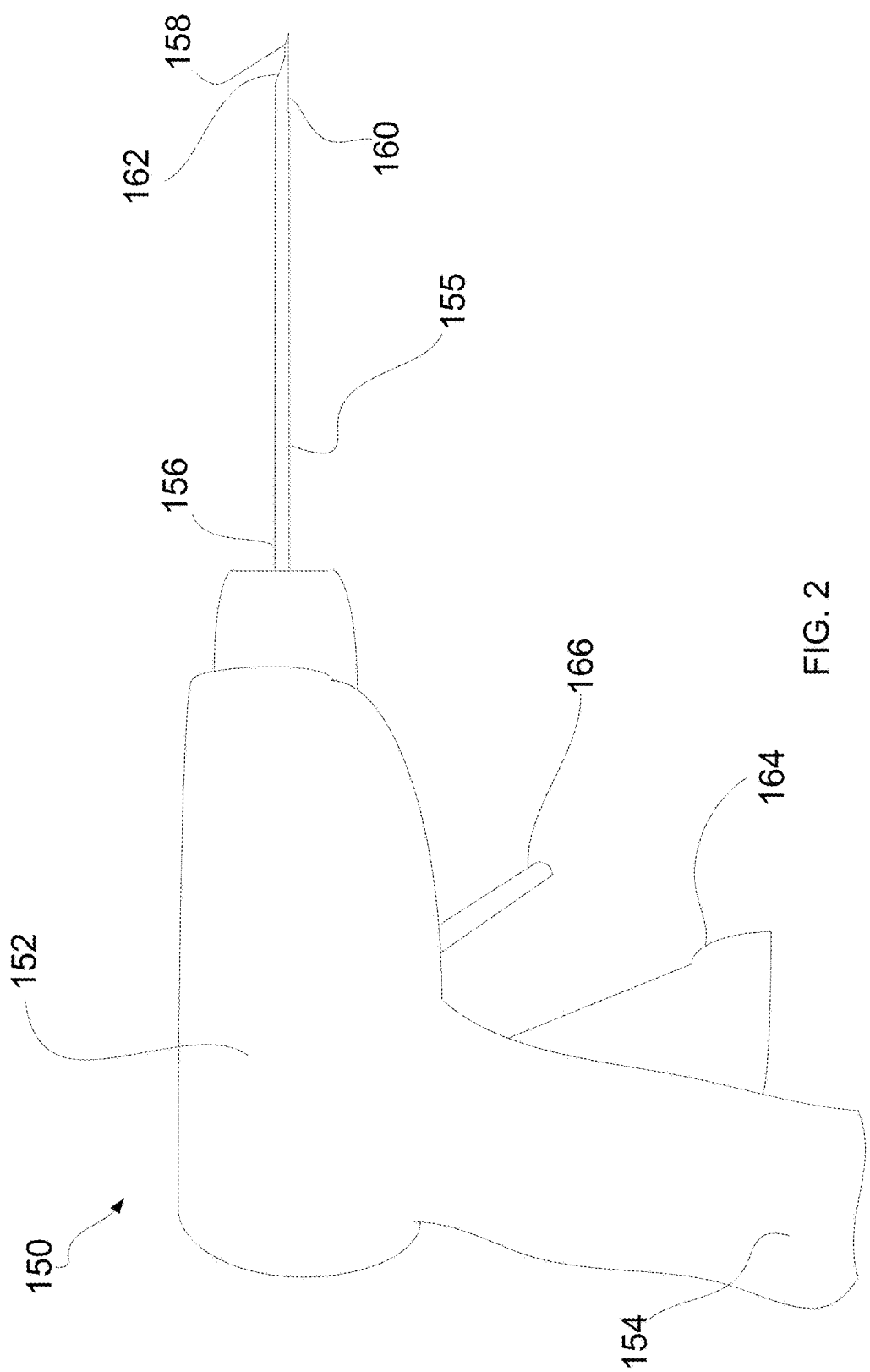
FIG. 2 is a side view of an implant inserter according to an embodiment of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

In describing and claiming the present disclosure, the following terminology will be used in accordance with the definitions set out below. As used in this specification and the appended claims, the singular forms "a," "an," and "the" include plural referents unless the context clearly dictates otherwise. As used in this specification and the appended claims, the terms "comprising," "including," "containing," "characterized by," and grammatical equivalents thereof are inclusive or open-ended terms that do not exclude additional, unrecited elements or method steps.

Applicant has invented an all-inside surgical repair technique and related implant that may provide the benefits of an inside-out repair, but without the associated drawbacks. In particular, the implant may be entirely formed of suture material, which allows the implant to be loaded into a cannula having a smaller outer diameter than was previously possible. The smaller outer diameter of the cannula may allow the implant to be employed on both the superior and inferior surfaces of a meniscus.

In an embodiment, the implant may comprise a strand member connected to, and extending from, a first anchoring member. The first anchoring member may be operable between a first configuration and a second configuration. In the first configuration, the first anchoring member may be substantially linear in shape. In the second configuration, the first anchoring member may deformed into a mass, such as a suture mass, as the strand member is placed under tension by a surgeon.

In an embodiment, the first anchoring member may have a diameter greater than a diameter of the strand member. In this regard, the first anchoring member may be formed of a first suture material and the strand member may be formed of a second suture material. The diameter of the first suture material of the first anchoring member may be greater than a diameter of the second suture material of the strand member.

In an embodiment, the first suture material may have a diameter between 0.3 and 0.7 millimeters, or about 0.5 millimeters, and the diameter of the second suture material may be between 0.2 and 0.4 millimeters, or about 0.3 millimeters. In an embodiment, ratio of the diameter of the first suture material to the diameter of the second suture material is between 1.5 and 1.8. The first anchoring member may have a length between 9 millimeters and 15 millimeters, or about 12 millimeters. In an embodiment, the strand member may comprise a looped portion having a self-locking surgical knot such that the strand member may be cinched tight by a surgeon.

In its second configuration, the first anchoring member may be deformed, collapsed or pulled, into a suture mass from its linear shape, when deployed by traction. In an embodiment, the suture mass may be S-shaped. In an embodiment, the suture mass may comprise multiple layers of suture material. The first anchor member may deployed from a linear shape into a suture mass in response to the strand member being placed under tension.

In an embodiment, the strand member comprises a first portion that passes through the first anchoring member, wherein the first portion is perpendicular to a longitudinal axis of the first anchoring member when the first anchoring member is in the first configuration. The strand member may further comprise a second portion that passes through the first anchoring member, where the first portion and the second portion are perpendicular to a longitudinal axis of the first anchoring member when the first anchoring member is in the first configuration. The strand member may further comprise a third portion, wherein the third portion extends along an exterior of the first anchoring member between the first portion and the second portion. In an embodiment, the strand member comprises a looped portion passing through the first anchoring member.

In an embodiment, the implant may comprise a second anchoring member interlaced by the strand member in addition to the first anchoring member. The second anchoring member may be operable between a first configuration and a second configuration, where the second anchoring member may be substantially linear in shape in the first configuration and may be deformed into a mass, such as a suture mass, in the second configuration. The second anchoring member may comprise a suture material having a diameter greater than a diameter of the strand member. The first anchor member and the second anchor member may be deployed from their first configuration to their second configuration in response to the strand member being placed under tension.

In an embodiment, the present disclosure may further comprise a system for repairing tears in soft tissue. The system may include an implant insertion device having a cannula defining an elongate, hollow tubular body having a tissue puncturing tip at a distal end and a handle or grip at its proximal end for receiving a hand of a surgeon. Disposed within the cannula may be an implant having a first anchoring member operable between a first configuration and a second configuration and a strand member connected to the first anchoring member. The first anchoring member may be operable between a first configuration and a second configuration in response to the strand member being placed under tension, where the first anchoring member may be substantially linear in shape in the first configuration and may be deformed into a mass, such as a suture mass, in the second configuration.

In an embodiment, the implant may further comprise a second anchoring member disposed within the cannula. The second anchoring member may be operable between a first configuration and a second configuration. The second anchoring member may also be operable between a first configuration and a second configuration in response to the strand member being placed under tension, where the second anchoring member may be substantially linear in shape in the first configuration and may be deformed into a mass, such as a suture mass, in the second configuration.

In an embodiment, the first anchoring member and the second anchoring member may be formed from a first suture material and the strand member may be formed from a second suture material. In an embodiment, the first suture material may have a diameter greater than a diameter of the second suture material. The first suture material may have a diameter between 0.3 and 0.7 millimeters, or about 0.5 millimeters, and the diameter of the second suture material may be between 0.2 and 0.4 millimeters, or about 0.3 millimeters. In an embodiment, a ratio of the diameter of the first suture material to the diameter of the second suture material may be between 1.5 and 1.8.

In an embodiment, the first anchoring member and the second anchoring member may have a length between 9 millimeters and 15 millimeters, or about 12 millimeters. The strand member may form a looped portion between the first anchoring member and the second anchoring member, and the strand member may have a self-locking surgical knot. A length of the looped portion of the strand member between the first anchoring member and the second anchoring member may be between 25 millimeters and 35 millimeters, or about 30 millimeters.

The system may further include a tissue-puncturing tip formed on the distal end of the cannula. The tissue-puncturing tip may be operable to pierce a superior or inferior surface of body tissue, such as a meniscus. The tissue-puncturing tip may form channels through the meniscus.

In an embodiment, the cannula may comprise a first bended portion defining a first angle. In an embodiment, the first angle may be between 25 degrees and 35 degrees, or about 30 degrees. In an embodiment, the first angle may be between 60 degrees and 70 degrees, or about 65 degrees. The cannula may comprise a second bended portion defining a second angle. In an embodiment, the second angle may be between 10 degrees and degrees, or about 15 degrees. In an embodiment, the tissue-puncturing tip may further comprise a bevel. The bevel may be bevel up or bevel down depending on the location of the tear on the meniscus. In an embodiment, the cannula may comprise an internal taper for feeding the implant.

The system may further include one or more push rods disposed in the cannula. The one or more push rods may be actuated by a surgeon to deploy the implant from the tissue-puncturing tip of the cannula. In an embodiment, a first push rod may deploy a first anchoring member from the distal end of the cannula and a second push rod may deploy the second anchoring member from the distal end of the cannula. In an embodiment, a single push rod may be utilized to deploy the first anchoring member and the second anchoring member from the distal end of the cannula. In an embodiment, the first anchoring member may be the lead anchoring member in the cannula and the second anchoring member may be the trailing anchoring member in the cannula.

In an embodiment, the tissue-puncturing tip of the cannula may puncture a first hole or channel through a surface of the soft tissue such that the tissue puncturing-tip extends from the opposite surface of the soft tissue (extracapsularly). The lead anchoring member may then be deployed from the cannula using a push rod on the opposite surface of the soft tissue (extracapsularly). The tissue-puncturing tip may then be withdrawn from the first hole or channel. The tissue-puncturing tip of the cannula may then puncture a second hole or channel through the surface of the soft tissue such that the tissue puncturing-tip extends from the opposite surface of the soft tissue (extracapsularly). The trailing anchoring member may then be deployed from the cannula using a push rod on the opposite surface of the soft tissue (extracapsularly). The tissue-puncturing tip may then be withdrawn from the second hole or channel. A lead of the strand member may then be tightened or cinched such that the lead anchoring member and the trailing anchoring member deploy to the second configuration to form a mass, such as a suture mass. The suture mass formed by the first and second anchoring members may be larger than the diameters of the channels formed by the tissue-puncturing tip to prevent pull out. The tightening or cinching of the strand member between the lead anchoring member and the trailing anchoring member may also reduce the tear in the soft tissue. A self-locking knot may prevent the loosening of the strand member. In an embodiment, the soft tissue may be a meniscus and the surface through which the tissue-puncturing tip is inserted may be a superior or inferior surface of the meniscus during an all-inside procedure. In an embodiment, an outer diameter of the cannula may be one of 1.5 millimeters or less, 1.6 millimeters or less, and 1.7 millimeters or less.

In an embodiment, a first anchoring member may extend along a longitudinal axis between a proximal, terminal end face and a distal, terminal end face, the first anchoring member having a sidewall which has a cross section that is generally cylindrical in shape (which, instead of the sidewall being generally cylindrical in shape, may also be any suitable shape, including but not limited to generally square, generally trapezoidal, or an at least four sided shape in which at least two of the sides are of a different length than the other sides) extending between the proximal, terminal end face and the distal, terminal end face, a strand pathway may extend through the first anchoring member, the strand pathway beginning at a proximal-most opening disposed on the generally cylindrical sidewall of the first anchoring member and ending at a distal-most opening disposed on the generally cylindrical sidewall of the first anchoring member, a strand member may extend along the strand pathway such that the strand member may pass through the proximal-most opening and the distal-most opening of the strand pathway such that the strand member does not pass through either of the proximal, terminal end face or the distal, terminal end face, wherein the first anchoring member is operable between a first configuration and a second configuration in response to actuation via the strand member, wherein the first anchoring member may be substantially linear in shape in the first configuration and is deformed into a mass in the second configuration.

It is to be understood that the team "linear" as used herein, shall be construed broadly to describe a member that is longitudinal and either generally straight or, if not generally straight, extending in a manner such that no portion of it forms an acute angle with itself than is less than or equal to ninety degrees.

In an embodiment, an implant may comprise a first anchoring member connected to a strand member, a cannula defining an elongate, hollow tubular body having a tissue puncturing tip at a distal end, wherein the implant may be configured and dimensioned to be loaded in the elongate, hollow tubular body of the cannula, a strand pathway may extend through the first anchoring member, the strand pathway beginning at a proximal-most opening disposed on the generally cylindrical sidewall of the first anchoring member and ending at a distal-most opening disposed on the generally cylindrical sidewall of the first anchoring member, a strand member may extend along the strand pathway such that the strand member passes through the proximal-most opening and the distal-most opening of the strand pathway such that the strand member does not pass through either of the proximal, terminal end face or the distal, terminal end face, wherein the first anchoring member may be operable between a first configuration and a second configuration, wherein the first anchoring member may be substantially linear in shape in the first configuration and is deformed into a mass in the second configuration.

In an embodiment, a method for repairing a tear in soft tissue, the soft tissue have a near surface and a far surface, may comprise: providing a cannula defining an elongate, hollow tubular body having a tissue-puncturing tip at a distal end and having an implant disposed within the elongate, hollow tubular body, the implant having a lead anchoring member and a trailing anchoring member connected by a strand member, the lead anchoring member comprising a suture material and the trailing anchoring member comprising a suture material; puncturing a first hole through the near surface of the soft tissue using the tissue puncturing tip such that the tissue puncturing tip extends from the far surface of the soft tissue; deploying the lead implant from the cannula on the far side of the soft tissue through the first hole; puncturing a second hole through the near surface of the soft tissue using the tissue puncturing tip such that the tissue puncturing tip extends from the far surface of the soft tissue; deploying the trailing implant from the cannula on the far side of the soft tissue through the second hole; tensioning the strand member to deform the first anchoring member and the second anchoring member into suture masses larger than a diameter of the first hole and the diameter of the second hole, respectively, and to close the tear; wherein the lead anchoring member extends along a longitudinal axis between a proximal, terminal end face and a distal, terminal end face; wherein the lead anchoring member includes a generally cylindrical sidewall extending between the proximal, terminal end face and the distal, terminal end face; wherein a strand pathway extends through the lead anchoring member, the strand pathway beginning at a proximal-most opening disposed on the generally cylindrical sidewall of the lead anchoring member and ending at a distal-most opening disposed on the generally cylindrical sidewall of lead anchoring member; wherein the strand member extends along the strand pathway such that the strand member passes through the proximal-most opening and the distal-most opening of the strand pathway such that the strand member does not pass through either of the proximal, terminal end face or the distal, terminal end face of the lead anchoring member.

Referring now to FIGS. 1A and 1B, there is depicted an all-suture implant 100 for use in soft tissue repair according to an embodiment of the present disclosure. The implant 100 may include a lead or first anchoring member 102 and a trailing or second anchoring member 104. The lead anchoring member 102 and the trailing anchoring member 104 may be interconnected by a strand member 106.

In an embodiment, the lead anchoring member 102 and the trailing anchoring member 104 may be formed of a flexible material. In an embodiment, the lead anchoring member 102 and the trailing anchoring member 104 may be formed of a suture material. In an embodiment, the suture material may be a #2 suture as is known to those having ordinary skill. In an embodiment, the lead anchoring member 102 and the trailing anchoring member 104 may have a diameter, D1, of between 0.3 and 0.7 millimeters, or 0.5 millimeters, or about 0.5 millimeters. Each of the lead anchoring member 102 and the trailing anchoring member 104 may comprise a longitudinal axis 108 and 110, respectively. As shown in FIGS. 1A and 1B, the lead anchoring member 102 and the trailing anchoring member 104 may be substantially linear in shape.

In an embodiment, the strand member 106 may be formed of a flexible material. In an embodiment, the strand member 106 may be formed of a suture material. In an embodiment, the suture material forming the strand member may be a #2-0 suture as is known to those having ordinary skill. In an embodiment, the strand member 106 may have a diameter of between 0.2 and 0.4 millimeters, or 0.3 millimeters, or about 0.3 millimeters. In an embodiment, the lead anchoring member 102, the trailing anchoring member 104, and the strand member 106 may be formed of a bioabsorbable suture material.

As will now be explained, the strand member 106 may be interlaced with the lead anchoring member 102 and the trailing anchoring member 104. In particular, a first lead 106A of the of the strand member 106 may enter a first channel 112 of the trailing anchoring member 104 and pass perpendicularly through its longitudinal axis 110 and exit the first channel 112 on the opposite side of the trailing anchoring member 104. The first lead 106A may then travel parallel to the axis 110 along the outside of the trailing anchoring member 104. The first lead 106A may then enter a second channel 114 of the trailing anchoring member 104 and pass perpendicularly through its longitudinal axis 110 and exit the second channel 114 on the opposite side of the trailing anchoring member 104. The first lead 106A may then travel parallel to the axis 110 along the outside of the trailing anchoring member 104. The first lead 106A may then enter a third channel 116 of the trailing anchoring member 104 and pass perpendicularly through its longitudinal axis 110 and exit the third channel 116 on the opposite side of the trailing anchoring member 104.

Next, the first lead 106A may then extend to the lead anchoring member 102. The first lead 106A may then enter a first channel 118 of the lead anchoring member 102 and pass perpendicularly through its longitudinal axis 108 and exit the first channel 118 on the opposite side of the lead anchoring member 102. The first lead 106A may then travel parallel to the axis 108 along the outside of the lead anchoring member 104. The first lead 106A may then enter a second channel 120 of the lead anchoring member 102 and pass perpendicularly through its longitudinal axis 108 and exit the second channel 120 on the opposite side of the lead anchoring member 102. The first lead 106A may then extend along the side of the lead anchoring member 102. The first lead 106A may then enter a third channel 122 of the lead anchoring member 102 and pass perpendicularly through its longitudinal axis 108 and exit the third channel 122 on the opposite side of the lead anchoring member 102. The third channel 122 of the lead anchoring member 102 may be perpendicular to the first channel 118 and the second channel 120 of the lead anchoring member 102.

Once the first lead 106A exits the third channel 122 of the lead anchoring member 102, the first lead 106A may follow the same pathway back to the entrance of the first channel 112 of the trailing anchoring member 104 where it may terminate in a second lead 106B. It will be appreciated that the self-locking knot 124 of the strand member 106 may define a looped (or double stranded) portion between the trailing anchoring member 104 and the lead anchoring member 102, with the bend of the looped portion being disposed in the third channel 122. It will be further appreciated that the self-locking knot 124 allows the looped portion formed by the strand member 106 to be cinched or tightened as a surgeon pulls on the first lead 106A (which overlaps or runs alongside part of the looped portion as shown clearly in FIGS. 6D and 7B) of the strand member 106, as will be explained in more detail hereinafter.

In an embodiment, the lead anchoring member 102 may extend between a proximal, terminal end face 102A and a distal, terminal end face 102B. In an embodiment, a length, L1, between the proximal, terminal end face 102A and the distal, terminal end face 102B may be between 9 millimeters and 15 millimeters, or about 12 millimeters. In an embodiment, a length, L2, between the proximal end 102A and the first channel 118 of the lead anchoring member 102 may be about 2 millimeters. In an embodiment, a length, L3, between the first channel 118 and the second channel 120 of the lead anchoring member 102 may be about 4 millimeters. In an embodiment, a length, L4, between the second channel 120 and the third channel 122 of the lead anchoring member 102 may be about 4 millimeters. In an embodiment, a length, L5, between the third channel 122 and the distal end 102B of the lead anchoring member 102 may be about 2 millimeters.

It will be appreciated that a strand pathway may be defined through the lead anchoring member 102. The strand pathway may begin at a proximal-most opening 113 disposed on a generally cylindrical sidewall 115 of the lead anchoring member 102 and ending at a distal-most opening 117 disposed on the generally cylindrical sidewall 115 of the lead anchoring member 102.

Referring now to FIG. 1A, it is to be understood that the term "proximal-most opening" as used herein, shall be construed to mean an opening that resides the closest distance to a proximal, terminal end face 104A of the anchoring member 104; the term "proximal-most opening" may also mean an opening that resides a distance from the proximal, terminal end face 104A that is substantially equal to a distance that a different opening resides from the proximal, terminal end face 104A; still further, the term "proximal-most opening" may mean, still in reference to FIG. 1A, an opening that the first lead 106A of the strand member 106 first enters an anchoring member when, for example, in FIG. 1A, viewing a strand direction of travel being from a proximal part of the anchoring member 104 toward the distal part—and as such opening 107 is the proximal-most opening and opening 109 the distal-most opening—even if neither of the two foregoing definitions of "proximal-most opening" applies. Similarly, the term "distal-most opening" as used herein, shall be construed to mean an opening that resides the closest distance to a distal, terminal end face 104B of the first anchoring member 104; the term "distal-most opening" may also mean an opening that resides a distance from the distal, terminal end face 104B that is substantially equal to a distance that a different opening resides from the distal, terminal end face 104B; still further, the term "distal-most opening" may mean, still in reference to FIG. 1A, an opening that the first lead 106A of the strand member 106 last exits from an anchoring member when, for example, in FIG. 1A, viewing a strand direction of travel being from a proximal part of the anchoring member 104 toward the distal part—and as such opening 107 is the proximal-most opening and opening 109 the distal-most opening—even if neither of the two foregoing definitions of "distal-most opening" applies.

The strand member 106 may extend along the strand pathway such that the strand member 106 passes through the proximal-most opening 113 and the distal-most opening 117 of the strand pathway such that the strand member 106 does not pass through either of the proximal, terminal end face 102A or the distal, terminal end face 102B of the lead anchoring member 102.

In an embodiment, the trailing anchoring member 104 may extend between the proximal, terminal end face 104A and a distal, terminal end face 104B. In an embodiment, a length, L6, between the proximal end 104A and the distal end 104B may be between 9 millimeters and 15 millimeters, or about 12 millimeters. In an embodiment, a length, L7, between the proximal end 104A and the first channel 112 of the trailing anchoring member 104 may be about 2 millimeters. In an embodiment, a length, L8, between the first channel 112 and the second channel 114 of the trailing anchoring member 104 may be about 4 millimeters. In an embodiment, a length, L9, between the second channel 114 and the third channel 116 of the trailing anchoring member 104 may be about 4 millimeters. In an embodiment, a length, L10, between the third channel 116 and the distal end 104B of the trailing anchoring member 104 may be about 2 millimeters. In an embodiment, a length, L11, between the leading implant 102 and the trailing implant 104 may be between 25 millimeters and 35 millimeters, or about 30 millimeters.

It will be appreciated that a strand pathway may be defined through the trailing anchoring member 104. The strand pathway may begin at a proximal-most opening 107 disposed on a generally cylindrical sidewall 111 of the trailing anchoring member 104 and ending at a distal-most opening 109 disposed on the generally cylindrical sidewall 111 of the trailing anchoring member 104.

The strand member 106 may extend along the strand pathway such that the strand member 106 passes through the proximal-most opening 107 and the distal-most opening 109 of the strand pathway such that the strand member 106 does not pass through either of the proximal, terminal end face 104A or the distal, terminal end face 104B of the trailing anchoring member 104.

Referring now to FIG. 2, there is depicted a surgical device 150 for surgically installing the implant 100 in a patient to repair soft tissue. The device 150 may include a body portion 152 having a handle or grip 154 extending therefrom. Extending from a forward portion of the body portion 152 may be a cannula 155 having a proximal end 156 and a distal end 158. Formed in the distal end 158 of the cannula 155 may be a tissue-puncturing tip 160. The tissue-puncturing tip 160 may include a beveled portion 162. As will be explained in more detail hereinafter, the implant 100 may be pre-loaded in the cannula 155. In an embodiment, the pre-loaded cannula 155 may be interchangeable with other pre-loaded cannulas to provide different cannula configurations.

As can be observed, the device 150 may include a first trigger 164 and a second trigger 166. The first trigger 164 and the second trigger 166 may be hand actuated by a surgeon holding the device 150 by the grip 154. The first trigger 164 may be operable to separately deploy the lead implant 102 and the trailing implant 104 from the cannula 155. The second trigger 166 may be operable to position the trailing implant 104 for deployment after the lead implant 102 has been deployed.

Referring now to FIGS. 2 and 3A-3D, where like reference numerals depict the same components, the cannula 155 may define an elongate, hollow tubular body having a tapered portion 172 disposed between a proximal passageway 174 and a distal passageway 176. The proximal passageway 174 may have a diameter greater than the distal passageway 176.

The first trigger 164 may be mechanically interconnected to a first push rod 168. Actuation of the first trigger 164 may cause the first push rod 168 to extend beyond the distal end 158 of the cannula 155. The second trigger 166 may be mechanically interconnected to a second push rod 170. Actuation of the second trigger 166 may cause the second push rod 170 to extend into the tapered portion 172 the cannula 155. Alternatively, in an embodiment, actuation of the second trigger 166 may cause the second push rod 170 to extend beyond the distal end 158 of the cannula 155.

Figure 3:
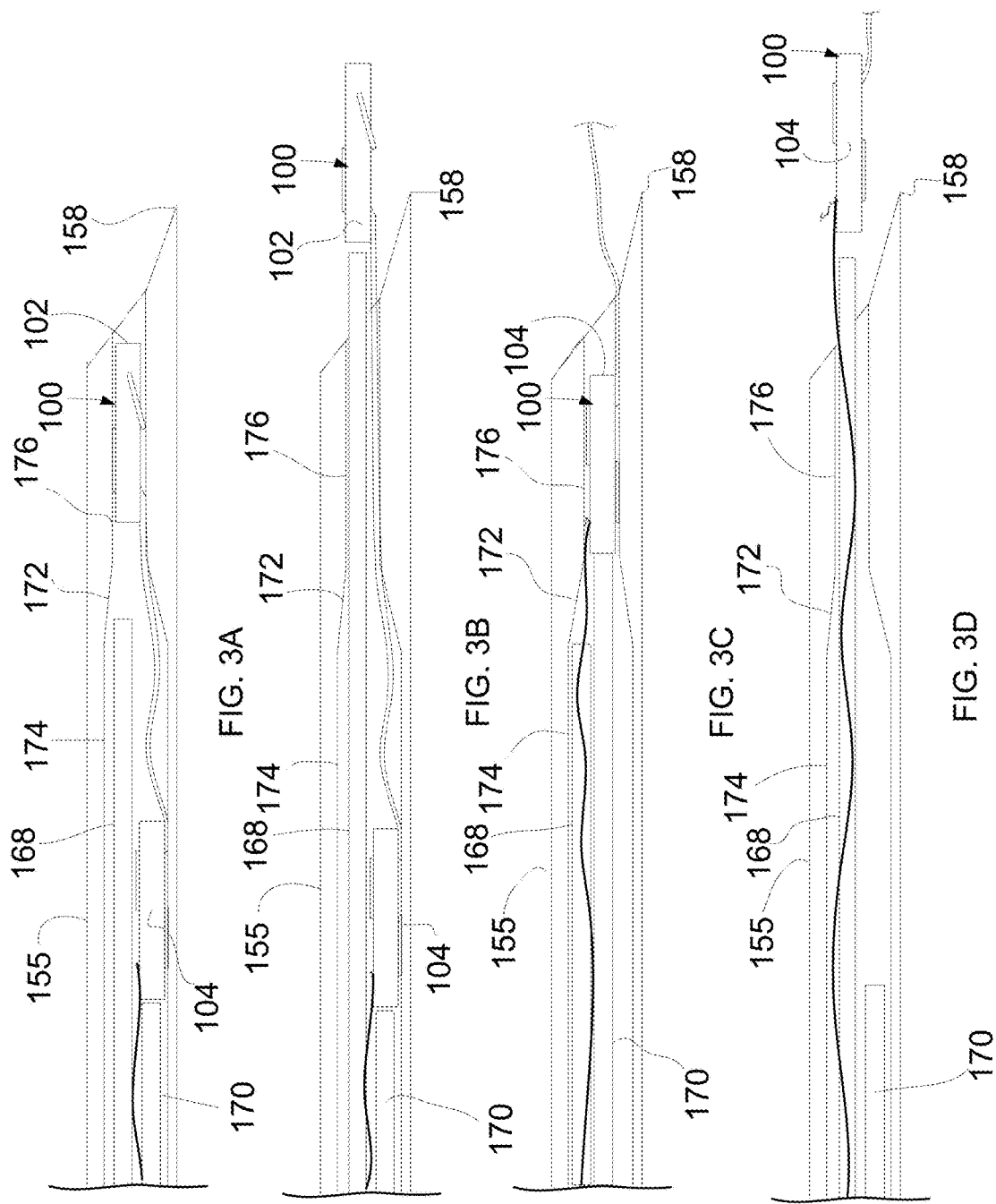
FIGS. 3A-3D depict an insertion procedure of the implant shown in FIG. 1 using the implant inserter shown in FIG. 2.

As perhaps best seen in FIGS. 3A-3D, there is depicted, generally, a process for deploying the implant 100 from the distal 158 end cannula 155 of the device 150 during a surgical procedure. In particular, FIG. 3A shows the implant 100 pre-loaded into the cannula 155 such that the lead anchoring member 102 may be positioned in the distal passageway 176 of the cannula 155 and the trailing anchoring member 104 may be positioned in the proximal passageway 174 of the cannula 155.

In FIG. 3B, the first push rod 168 is extended beyond the distal end 158 of the cannula 155 to deploy the lead anchoring member 102 from the distal passageway 176 in response to actuation of the first trigger 164 of the device 150. After deploying the lead anchoring member 102, the rod 168 may be moved back into its original position as shown in FIG. 3A by a resilient member (not shown). In FIG. 3C, the second push rod 170 is extended to move the trailing anchoring member 104 into position in the distal passageway 176 from the proximal passageway 174 in response to actuation of the second trigger 166 of the device 150.

After moving the trailing anchoring member 104 into the distal passageway 176, a resilient member (not shown) may move the rod 170 back into its original position as shown in FIG. 3A. In FIG. 3D, the first push rod 168 is again extended beyond the distal end 158 of the cannula 155 to deploy the trailing anchoring member 104 from the distal passageway 176 of the cannula 155 in response to actuation of the first trigger 164 of the device 150.

Figure 4:
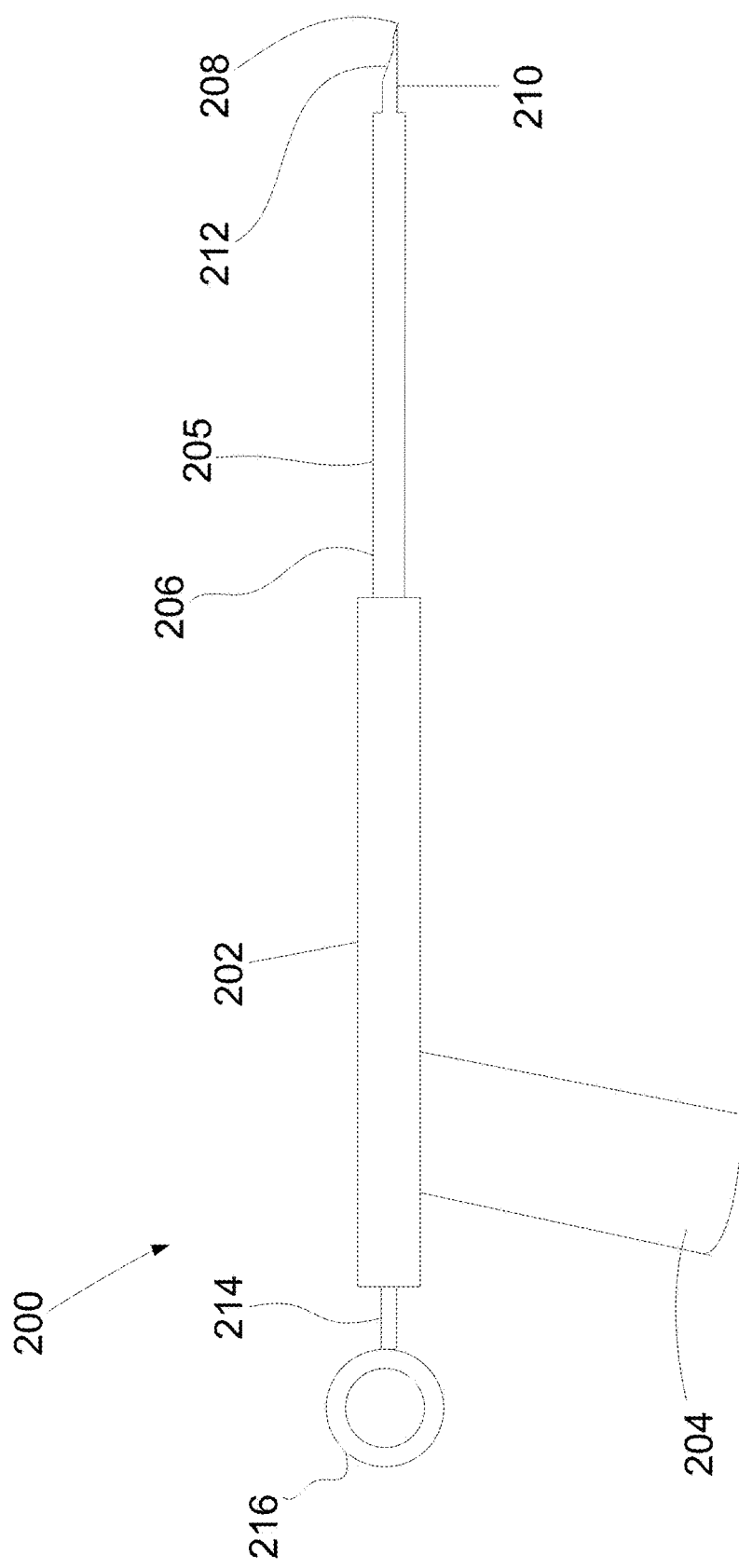
FIG. 4 is a side view of an implant inserter according to an embodiment of the present disclosure.

Referring now to FIG. 4, there is depicted a surgical device 200 for surgically installing the implant 100 in a patient to repair soft tissue. The device 200 may include a body portion 202 having a handle or grip 204 extending therefrom. Extending from a forward portion of the body portion 202 may be a cannula 205 having a proximal end 206 and a distal end 208. Formed adjacent the distal end 208 of the cannula 205 may be a tissue-puncturing tip 210. The tissue-puncturing tip 210 may include a beveled portion 212. As will be explained in more detail hereinafter, the implant 100 may be pre-loaded in the cannula 205. In an embodiment, the pre-loaded cannula 205 may be interchangeable with other pre-loaded cannulas to provide different cannula configurations.

A push rod 214 may extend into a proximal end of the body portion 202 of the device 200. The push rod 214 may include a ring portion 216 for receiving and capturing a digit of a surgeon. As will be explained below, a surgeon may actuate the push rod 214 to deploy the implant 100 from the distal end 208 of the cannula 205 into soft tissue.

In particular, as shown in FIGS. 4 and 5A-5D, there is depicted, generally, a process for deploying the implant 100 from the distal end 208 of the cannula 205 of the device 200 during a surgical procedure. The cannula 205 may define an elongate, hollow tubular body having an interior passageway 224. The passageway 224 may include a tapered portion 226 that separates a proximal passageway 220 and a distal passageway 218. The distal passageway 218 may have a diameter smaller than a diameter of the proximal passageway 220.

An outer portion of the cannula 205 may include a shoulder 228, from which extends the tissue-puncturing tip 210. The tip 210 may have a length, L13, that extends from the shoulder 228 to the beveled portion 212 that is about 14 millimeters. A length, L14, of the beveled portion 212 may be about 2 millimeters. A length, L15, between the beveled portion 212 and the distal end 208 may also be about 2 millimeters. A length, L12, between the shoulder 228 and the start of the tapered portion 226 may be about 4 millimeters. Thus, the overall length of the tissue-puncturing tip 210 may be about 18 millimeters (L13+L14+L15). As used herein, the term "about" means within +/−15% of the stated value.

In an embodiment, a diameter, D3, of the tissue-puncturing tip 210 may be one of 1.5 millimeters or less, 1.6 millimeters or less, and 1.7 millimeters or less. A diameter, D4, of the cannula 205 behind the shoulder 228 may be about 2.2 millimeters. It will be appreciated that the shoulder 228 may control the depth of insertion of the tissue-puncturing tip 210 into soft tissue. In particular, the shoulder 228 may serve as a depth stop that abuts against the soft tissue to stop the forward progress of the tip 210.

As can be observed, FIG. 5A shows the implant 100 pre-loaded into the cannula 205 such that the lead anchoring member 102 may be positioned in the distal passageway 218 of the cannula 205 and the trailing anchoring member 104 may be positioned in the proximal passageway 220 of the cannula 205.

In FIG. 5B, the push rod 214 is extended beyond the distal end 208 of the cannula 205 by a surgeon to deploy the lead anchoring member 102 from the distal passageway 218 in response to manual actuation of the ring 216 of the device 200 (see FIG. 4). After deploying the lead anchoring member 102, the rod 214 may be moved back into its original position as shown in FIG. 5A by a resilient member (not shown) or by the surgeon. In FIG. 5C, the push rod 214 may be moved behind the trailing anchoring member 104 by the surgeon. In FIG. 5D, the push rod 214 may again be extended beyond the distal end 208 of the cannula 205 to deploy the trailing anchoring member 104 from the distal passageway 218 of the cannula 205 in response to actuation of the ring 216 of the device 200. The tapered portion 226 may guide the trailing anchoring member 104.

Referring now to FIGS. 6A-6F, there is depicted an all-inside method of surgical repair of a tear 252 in a meniscus 250 of a patient according to an embodiment of the present disclosure using the device 200. The meniscus 250 may have a superior surface 254, an inferior surface 256, and an outside surface 258. It will be appreciated that the repair may also be performed using the device 150, or any other type of cannulated device capable of deploying the implant 100. In an embodiment, the implant 100 may be pre-loaded into the cannula 205 of the device 200. It will be appreciated that the method shown in FIGS. 6A-6F may be performed using arthrosporic surgical techniques as known to those of ordinary skill.

Figure 6A:
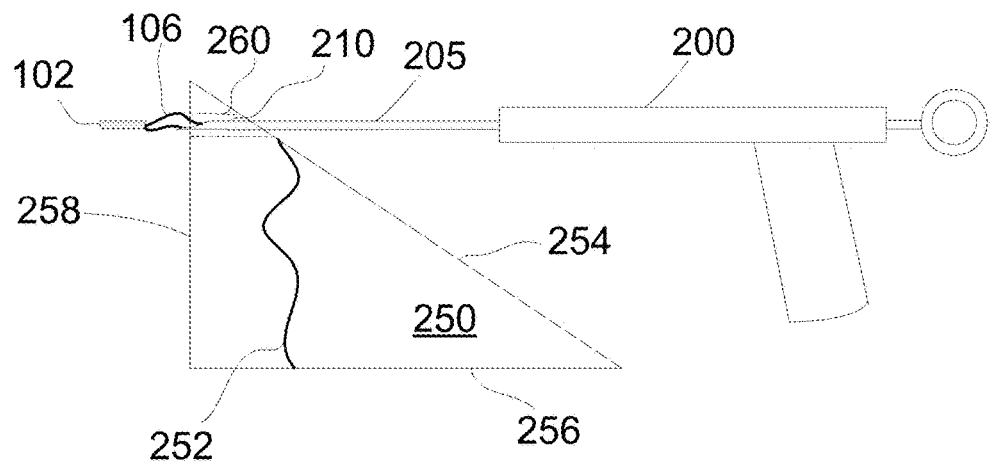
Figure 6B:
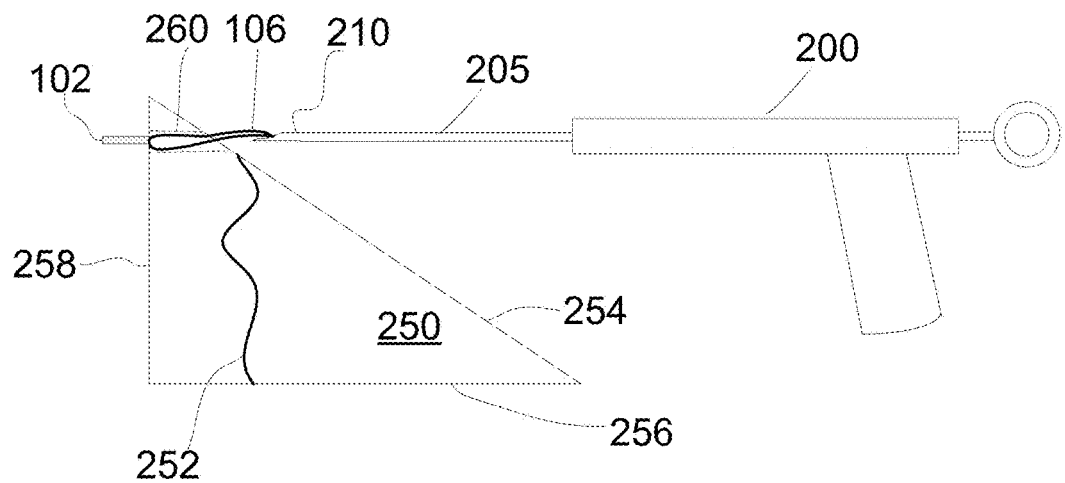

In FIG. 6A, the tissue-puncturing tip 210 of the device 200 is utilized to form a first channel 260 extending from the superior surface 254 to the outside surface 258 of the meniscus 250. The lead anchoring member 102 is then deployed from the cannula 205 by the surgeon (as shown in FIG. 5B). As shown in FIG. 6B, once the lead anchoring member 102 has been deployed, the tip 210 is withdrawn from the first channel 260 with the looped portion of the stand member 106 also exiting the first channel 260. As shown in FIG. 6C, the tissue-puncturing tip 210 of the device 250 is utilized to form a second channel 262 extending from the superior surface 254 to the outside surface 258 of the meniscus 250. The trailing anchoring member 104 is then deployed from the cannula 205 by the surgeon (as shown in FIG. 5D). As shown in FIG. 6D, once the trailing anchoring member 104 has been deployed, the tip 210 is withdrawn from the second channel 262 with the looped portion of the stand member 106 extending between the lead anchoring member 102 and the trailing anchoring member 104. The first lead 106A of the strand member 106 may also exit the second channel 262 on the inside of the meniscus 250. As clearly shown in FIG. 6D, the first lead 106A of the strand member 106 may overlap at least part of the length of the strand member 106 that extends from the lead anchoring member 102 to the trailing anchoring member 104. For example, as also clearly shown in FIG. 6D, the first lead 106A of the strand member 106 may overlap or run alongside at least part of the looped portion of the strand member 106.

As shown in FIG. 6E, the surgeon may then place the first lead 106A in tension to thereby cinch the looped portion of the strand member 106 extending between the lead anchoring member 102 and the trailing anchoring member 104. As the looped portion of the strand member 106 is cinched, each of the lead anchoring member 102 and the trailing anchoring member 104 may deform from a first configuration to a second configuration. In particular, in the first configuration, the lead anchoring member 102 and the trailing anchoring member 104 may be substantially linear in shape as shown in FIGS. 6A-6D. In the second configuration, the lead anchoring member 102 and the trailing anchoring member 104 may deform into a mass, such as a suture mass, as shown in FIG. 6E. The self-locking knot 124 (see FIGS. 1A and 1B) may prevent the looped portion of the strand member 106 from loosening. In an embodiment, a knot pusher may be utilized to cinch the looped portion of the strand member 106. The first lead 106A may be trimmed from the inside of the joint cavity so as not to interfere with the articulation of the knee joint. As shown in FIG. 6F, a second implant 100 may also be installed using the device 200 from the inferior surface 256 of the meniscus 250 in a similar manner as shown in FIGS. 6A-6E.

Figure 7A:
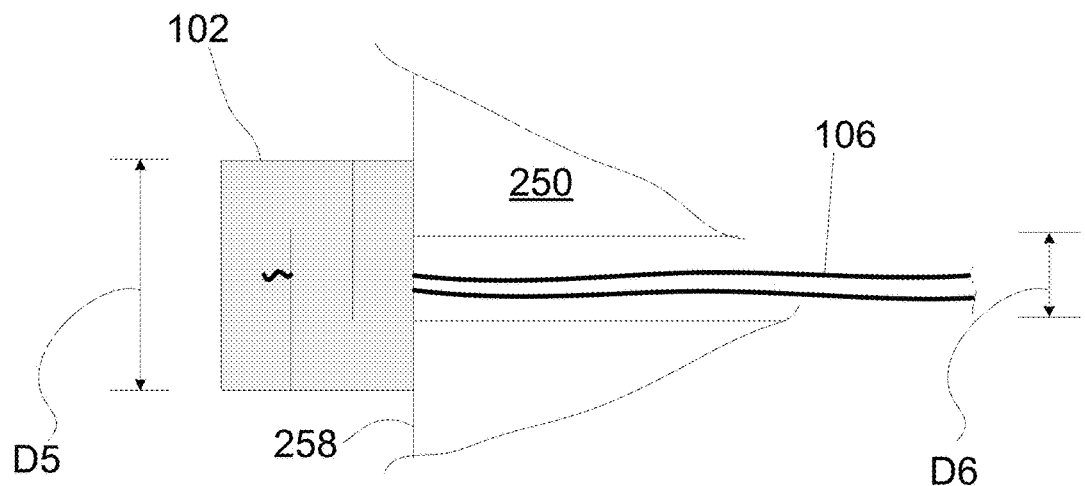
FIG. 7A depicts a lead anchor of the implant shown in FIG. 1 in the collapsed position.
Figure 7B:
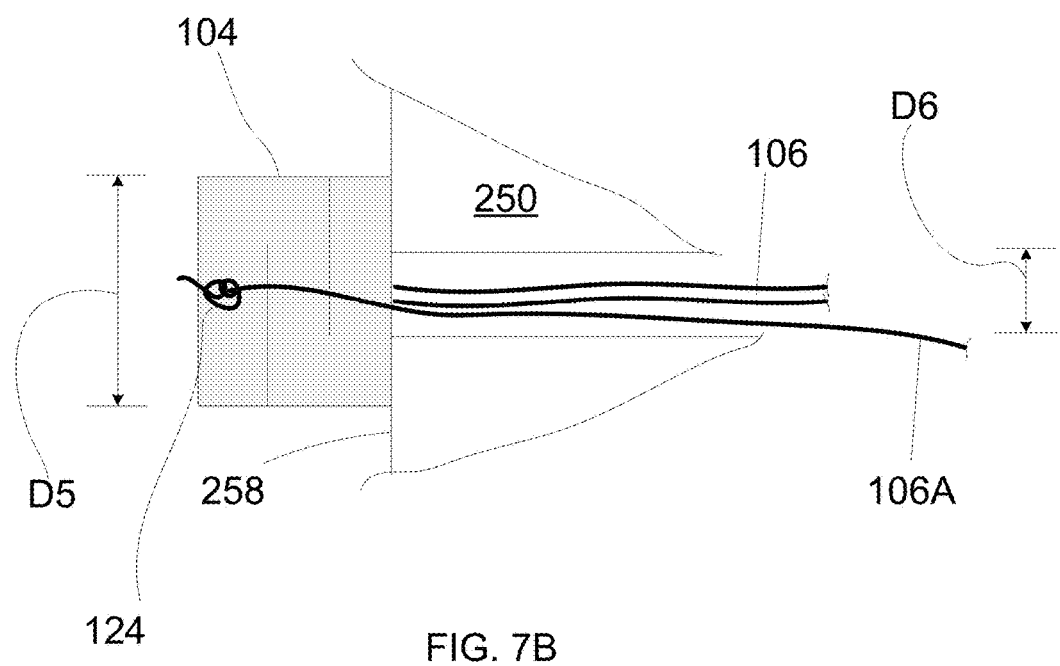
FIG. 7B depicts a trailing anchor of the implant shown in FIG. 1 in the collapsed position.

Referring now to FIGS. 7A and 7B, there is shown in more detail the deployment of the lead anchoring member 102 and the trailing anchoring member 104, respectively, of the implant 100 according to an embodiment of the present disclosure. In particular, the tightening of the looped portion of the strand member 106 using the first lead 106A causes the lead anchoring member 102 to deform into a suture mass (second configuration) from a substantially linear shape (first configuration). Likewise, the tightening of the looped portion of the strand member 106 using the first lead 106A causes the trailing anchoring member 104 to deform into a suture mass (second configuration) from a substantially linear shape (first configuration). The suture masses are located extracapsularly on the outside surface 258 of the meniscus 250. The self-locking knot 124 prevents the looped portion of the strand member 106 from loosening. It will be noted that the knot 124 may be located extracapsularly so as not to interfere with articulation of the joint. For example, as clearly shown in FIG. 7B, the knot 124 may be located outside of and near the outside surface 258 (also referred to as "far surface" of the far side) of the meniscus 250, and abutting the trailing anchoring member 104. Also as clearly shown in FIGS. 6D, 7A and 7B, the knot 124 may be disposed against and in contact with one of either the lead (or first) anchoring member 102 and the trailing (or second) anchoring member 104.

In the second configuration, the lead anchoring member 102 and the trailing anchoring member 104 may each form a suture mass, such as an S-shaped suture mass, having multiple layers due to the configuration of the interlacing of the stand member 106. For example, regarding the S-shaped suture mass, as clearly shown in FIGS. 7A and 7B, the S-shaped suture mass includes three (3) segments and two (2) folds, which could be referred to as a "three-two fold configuration." In an embodiment, a diameter, D5, of each of the suture masses formed by the lead anchoring member 102 and the trailing anchoring member 104 may be between 3 millimeters and 5 millimeters, or 4 millimeters, or about 4 millimeters, while the diameters, D6, of the first channel 260 and the second channel 262 may be about 1.5 millimeters. Thus, the diameters of the suture masses formed by the lead anchoring member 102 and the trailing anchoring member 104 prevent them from being pulled back through the first channel 260 and the second channel 262, respectively, as the looped portion of the strand member 106 is cinched tight by the surgeon tensioning the first lead 106A.

Figure 8:
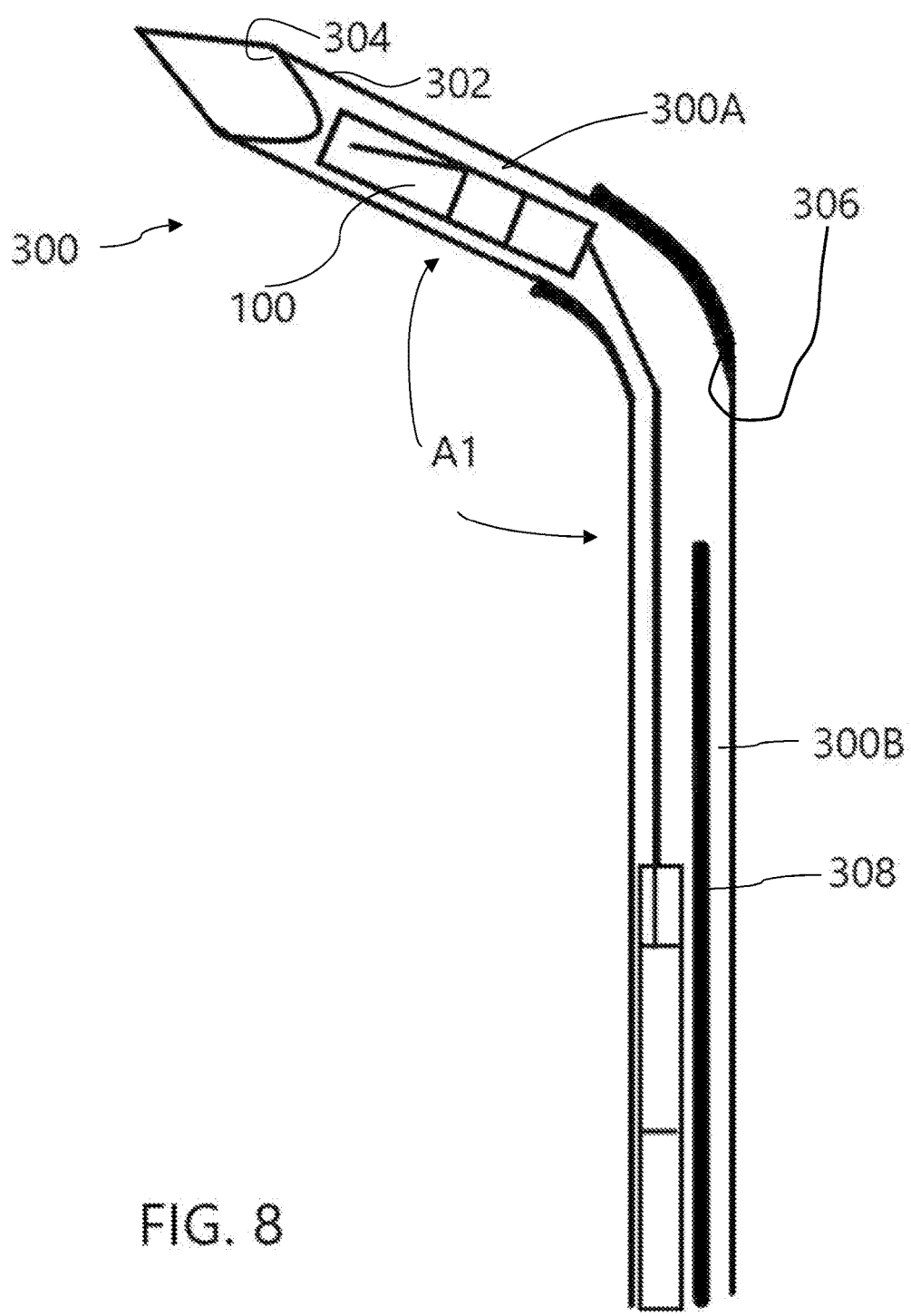
FIG. 8 depicts a cross sectional, top view of a cannulated implant inserter tip according to an embodiment of the present disclosure.

Referring now to FIG. 8, there is depicted a cannula 300 with a pre-loaded implant 100 according to an embodiment of the present disclosure. The cannula 300 may be utilized with the devices 150 and 200 shown in FIGS. 2 and 5, respectively. The cannula 300 may include a tissue-puncturing tip 302 having a beveled portion 304. The cannula 300 may include a first portion 300A and a second portion 300B. The first portion 300A and the second portion 300B may define bended portion having an angle, A1. In an embodiment, the angle, A1, may be between 60 degrees and 70 degrees, or about 65 degrees. The beveled portion 304 may face up or down to allow access to both the superior and inferior surfaces of the midbodies of either meniscus. In particular, bevel-up may allow access to the left superior/right inferior surface of a meniscus. Bevel-down may allow access to the right superior/left inferior surface of a meniscus. In an embodiment, the cannula 300 may have an internal taper 306 for feeding the implant 100 using a push rod 308 in the manner previously explained.

Figures 9A, 9B:
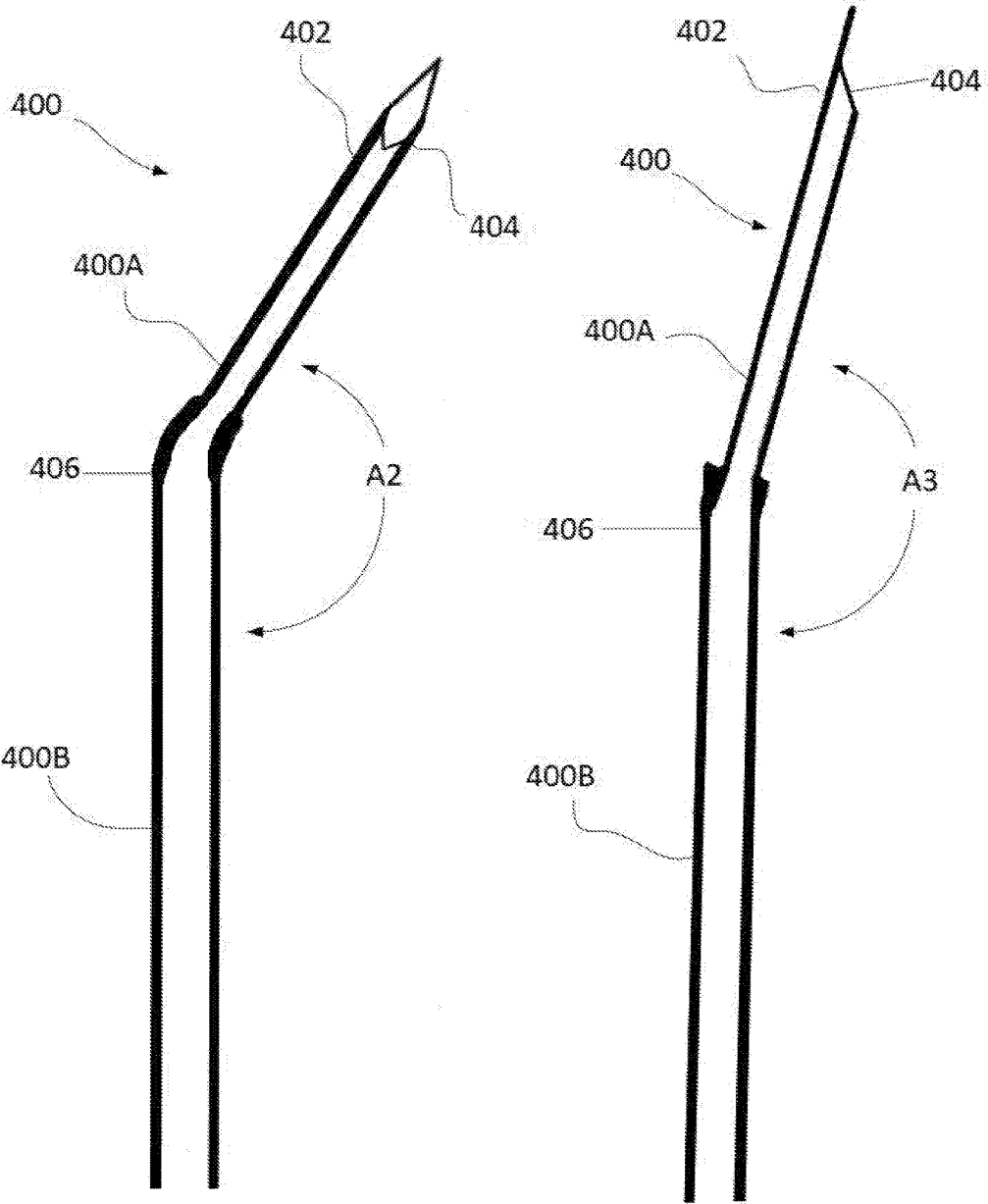
FIG. 9A depicts a cross sectional, top view of a cannulated implant inserter tip according to an embodiment of the present disclosure.
FIG. 9B depicts a cross sectional, side view of the implant inserter tip shown in FIG. 9A.

Referring now to FIGS. 9A and 9B, there is depicted a cannula 400 for use with an implant 100 according to an embodiment of the present disclosure. The cannula 400 may be utilized with the devices 150 and 200 shown in FIGS. 2 and 5, respectively. The cannula 400 may include a tissue-puncturing tip 402 having a beveled portion 404. The cannula 400 may include a first portion 400A and a second portion 400B. The first portion 400A and the second portion 400B may define first bended portion having an angle, A2. In an embodiment, the angle, A2, may be between 25 degrees and 35 degrees, or about 30 degrees. In an embodiment, the angle, A2, may be either right or left. The first portion 400A and the second portion 400B may define a second bended portion having an angle, A3. In an embodiment, the angle, A3, may be between 10 degrees and 20 degrees, or about 15 degrees.

It will be appreciated that the beveled portion 404 may face up or down. In particular, bevel-up may allow access to the right posterior inferior or the left posterior superior surfaces of a meniscus. Bevel-down may allow access to the left posterior inferior or the right posterior superior surfaces of a meniscus. In an embodiment, the cannula 400 may have an internal taper 406 for feeding an implant 100 using a push rod in the manner previously explained.

It will be appreciated that an implant according to an embodiment of the present disclosure may comprise two 12 millimeter sections of #2 suture, i.e., anchoring members, connected by a 30 millimeter loop of 2-0 suture, which is delivered antegrade through the meniscus, and which, when deployed by traction, deforms into an S-shaped suture mass extracapsularly. It will be appreciated that the actual size of the suture (for the 12 millimeter anchor) should have no bearing on the pull-out strength of the construct, since that is determined more by the ratio of the deployed suture anchor diameter to the insertion channel diameter, than by the tensile strength of the suture used. Since #2 suture alone fits down the cannula of an 18 gauge needle, which has a diameter of 1.27 millimeter, so with the added bulk of the 2-0 suture loop, using #2 suture should allow for the use of a cannulated inserter of approximately 1.5 mm diameter (thus less insult to the tissue). In contrast, the use of #5 suture as in the prior art requires a cannula of about 1.9 millimeters. A self-locking knot is delivered with the second implant.

It will be appreciates that the use of a small diameter all-suture implant allows for flexibility in deployment. In other words, the implant can be deployed with little resistance through various curved cannulas which can reach all aspects of the meniscus, just like the zone-specific cannulas mentioned previously. The "anterior" cannulas, which have about a 65 degree curve, may access the midbody of the meniscus, and may include one "bevel-up" and one "bevel-down" model, to allow access to both the superior and inferior surfaces of either meniscus. The "posterior" cannulas may have a gentler 30 degree curve (either left or right), but also a slight 15 degree upwards curve to allow access behind the femoral condyle. The present invention contemplates four posterior cannulas: left posterior (bevel-up and bevel-down) and right posterior (bevel-up and bevel-down). The tissue-puncturing tip of the cannula is 14 millimeter from the mouth of the needle to a shoulder, where the diameter increases from 1.5 to 2.2 millimeters, allowing control of the depth of insertion, and assuring deployment of the device deep to the capsule. Further, the distal 2 millimeters tapers to a cutting needle tip allowing the meniscus fragment to be manipulated and reduced prior to passage of the needle through the tear. The bevel may be a rounded, non-cutting surface, so the tip acts more like a tapered needle, leaving a lesser permanent channel through the meniscus tissue, and thereby improving the pullout strength of the implant. Internally, the barrel of the cannula may taper towards the distal end to allow for reliable implant feeding, and also for the nitinol wire pusher to reset for deployment of the trailing implant. The exact location of an internal taper in the cannula should be such that, as the tip is retracted and repositioned after deployment of the leading implant, the trailing implant feeds through the taper into the distal tip.

In an embodiment, the six different cannulas mentioned above may be packaged preloaded, and snapped onto a single disposable "gun" for each case. In an embodiment, each implant could be a separate disposable product. A pistol grip device, could be used, but from an ergonomic perspective, a cylindrical handle might allow more facile maneuver during the repair process. The inserter handle should be simple in design, with a spring-loaded plunger (the excursion of which should be calculated such that it retracts the thin nitinol wire after deploying the first implant to a point just behind the second implant); also, a safety catch must be released prior to deploying each implant, to prevent an inadvertent deployment during manipulation of the device.

In short, the meniscal repair device and insertion system outlined herein brings something entirely new to the vast meniscal repair market. The implant is small, flexible, and strong. It can be effectively deployed throughout the entire meniscus. The small diameter needle causes less insult to the meniscal tissue. And most importantly, it may allow an all-inside technique to accomplish a truly anatomic repair of the meniscus.

Those having ordinary skill in the relevant art will appreciate the advantages provide by the features of the present disclosure. For example, it is a feature of the present disclosure to provide an all-suture implant for use in soft tissue repair. Another feature of the present disclosure to provide such an implant with anchoring members that are interconnected by a loop. It is a further feature of the present disclosure, in accordance with one aspect thereof, to provide a device with a cannula, where the implant is pre-loaded into the cannula.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An apparatus for repairing tears in soft tissue, comprising:
   a first anchoring member having a strand pathway extending therethrough, wherein the first anchoring member is operable between a first configuration and a second configuration, wherein the first anchoring member is substantially linear in shape in the first configuration and is deformed into a mass in the second configuration, and wherein the strand pathway of the first anchoring member includes a first channel and a second channel, wherein the first and second channels are non-parallel when the first anchoring member is in the first configuration;
   a second anchoring member having a strand pathway extending therethrough;
   a strand member extending along the strand pathway of the first anchoring member and the strand pathway of the second anchoring member, the strand member having a first lead and a second lead, such that a length of the strand member extends from the first anchoring member to the second anchoring member; and
   a knot formed in the strand member;
   wherein only one of the first lead and the second lead is positioned to, and does, exit the knot and overlap at least part of said length of the strand member extending between the first anchoring member and the second anchoring member, such that said overlap occurs after said one of said first lead and said second lead exits the knot.

2. The apparatus of claim 1, wherein said knot is a self-locking knot.

3. The apparatus of claim 1, wherein said knot is disposed against and in contact with one of said first and second anchoring members.

4. The apparatus of claim 1, wherein the first anchoring member comprises a first suture material and the strand member comprises a second suture material.

5. The apparatus of claim 4, wherein the first suture material has a diameter greater than a diameter of the second suture material.

6. The apparatus of claim 4, wherein the first anchoring member has a length between 9 millimeters and 15 millimeters.

7. The apparatus of claim 5, wherein the first suture material has a diameter between 0.3 and 0.7 millimeters, or about 0.5 millimeters.

8. The apparatus of claim 5, wherein a ratio of the diameter of the first suture material to the diameter of the second suture material is between 1.5 and 1.8.

9. The apparatus of claim 7, wherein the diameter of the second suture material is between 0.2 and 0.4 millimeters, or about 0.3 millimeters.

10. The apparatus of claim 1, wherein the strand member defines a looped portion.

11. The apparatus of claim 1, wherein the mass comprises the first anchoring member deformed into an S-shaped suture mass.

12. The apparatus of claim 11, wherein the strand pathway of the first anchoring member has a first opening and a second opening disposed on the sidewall.

13. The apparatus of claim 12, wherein the first opening is a proximal-most opening on the first anchoring member and the second opening is a distal-most opening on the first anchoring member.

14. The apparatus of claim 13, wherein the knot is located proximate the proximal-most opening of the strand pathway of the first anchoring member.

15. The apparatus of claim 1, wherein the first anchoring member extends along a longitudinal axis between a proximal, terminal end face and a distal, terminal end face, having a sidewall comprising a non-rectangular cross section and extending between the proximal, terminal end face and the distal, terminal end face.

16. The apparatus of claim 15, wherein the sidewall of the first anchoring member comprises a cross sectional shape that is selected from the group consisting of:
generally cylindrical, generally trapezoidal, and an at least four sided shape having sides in which at least two of the sides are of a different length than the other sides.

17. The apparatus of claim 15, wherein the strand pathway of the first anchoring member comprises a first portion that is perpendicular to the longitudinal axis of the first anchoring member when the first anchoring member is in the first configuration.

18. The apparatus of claim 17, wherein the strand pathway of the first anchoring member further comprises a second portion that passes through the first anchoring member.

19. The apparatus of claim 18, wherein the first portion and the second portion are perpendicular to a longitudinal axis of the first anchoring member when the first anchoring member is in the first configuration.

20. The apparatus of claim 18, wherein the strand pathway of the first anchoring member further comprises a third portion, wherein the third portion extends along an exterior of the first anchoring member between the first portion and the second portion.

21. An apparatus for repairing tears in soft tissue, comprising:
a first anchoring member having a strand pathway; and
a strand member extending along the strand pathway of the first anchoring member;
wherein the first anchoring member is operable between a first, extended, configuration and a second configuration in response to actuation of the strand member;
wherein the first configuration enables the anchoring member to pass completely through an opening in the soft tissue, and the second configuration comprises the first anchoring member deformed into an S-shaped suture mass, such that the first anchoring member cannot enter the opening in the soft tissue, and wherein the strand pathway of the first anchoring member includes a first channel and a second channel, wherein the first and second channels are non-parallel when the first anchoring member is in the first configuration.

22. The apparatus of claim 21, wherein the S-shaped suture mass comprises three segments and two folds.

23. The apparatus of claim 21, wherein the S-shaped suture mass comprises a three-two fold configuration.

24. The apparatus of claim 21, wherein the first anchoring member comprises a first suture material and the strand member comprises a second suture material.

25. The apparatus of claim 24, wherein the first suture material has a diameter greater than a diameter of the second suture material.

26. The apparatus of claim 25, wherein the first suture material has a diameter between 0.3 and 0.7 millimeters, or about 0.5 millimeters.

27. The apparatus of claim 25, wherein a ratio of the diameter of the first suture material to the diameter of the second suture material is between 1.5 and 1.8.

28. The apparatus of claim 26, wherein the diameter of the second suture material is between 0.2 and 0.4 millimeters, or about 0.3 millimeters.

29. The apparatus of claim 21, wherein the first anchoring member has a length between 9 millimeters and 15 millimeters.

30. The apparatus of claim 21, wherein the strand member defines a looped portion.

31. An apparatus for repairing tears in soft tissue, comprising:
a first anchoring member having a strand pathway extending therethrough;
a second anchoring member having a strand pathway extending therethrough; and,
a strand member extending along the strand pathway of the first anchoring member and the strand pathway of the second anchoring member, the strand member forming a bend and following back along the strand pathway of the second anchoring member and the strand pathway of the first anchoring member, thereby forming a looped portion;
wherein the first anchoring member is operable between a first configuration and a second configuration in response to actuation of the strand member, wherein the diameter of the first anchor is narrower in the first configuration than an opening in the soft tissue and the shape of the first anchor is substantially linear, to thereby enable the first anchoring member to pass completely through the opening in the soft tissue, and the first anchor is deformed in the second configuration to thereby prevent the first anchoring member from entering the opening in the soft tissue and wherein the strand pathway of the first anchoring member includes a first channel and a second channel, wherein the first and second channels are non-parallel when the first anchoring member is in the first configuration; and
wherein the looped portion of the strand member extends between the first anchoring member and the second anchoring member.

32. The apparatus of claim 31, further comprising:
a cannula defining an elongate, hollow tubular body having a tissue puncturing tip at a distal end;
wherein the first anchoring member, the second anchoring member, and the strand member are configured and dimensioned to be pre-loaded in the elongate, hollow tubular body of the cannula.

33. The apparatus of claim 32, wherein an outer diameter of the cannula is less than 1.6 millimeters.

34. The apparatus of claim 32, further comprising a push rod positioned in the cannula and operable to deploy the first anchoring member from the tissue puncturing tip.

35. The apparatus of claim 34, wherein the cannula further comprises a bended portion defining an angle.

36. The apparatus of claim 35, wherein the angle is between 25 degrees and 35 degrees.

37. The apparatus of claim 35, wherein the angle is about 30 degrees.

38. The apparatus of claim 35, wherein the angle is between 60 degrees and 70 degrees.

39. The apparatus of claim 35, wherein the angle is about 65 degrees.

40. The apparatus of claim 31, wherein the first anchoring member comprises a first suture material and the strand member comprises a second suture material, and wherein the first suture material has a diameter greater than a diameter of the second suture material, wherein a ratio of the diameter of the first suture material to the diameter of the second suture material is between 1.5 and 1.8.

41. The apparatus of claim 31, wherein the first anchoring member has a length between 9 millimeters and 15 millimeters.

42. The apparatus of claim 31, wherein the looped portion of the strand member is configured and arranged to be cinched as tension is applied to the strand member.

43. The apparatus of claim 31, wherein the first anchoring member is deployed from the first configuration to the second configuration in response to the strand member being placed in tension.

44. The apparatus of claim 31, wherein the strand member further comprises a knot.

45. The apparatus of claim 31, wherein the strand member is connected to, and extends from, the second anchoring member, wherein the second anchoring member is operable between a first configuration and a second configuration, and wherein the second anchoring member is substantially linear in shape in its first configuration and is deformed into a mass in its second configuration.

46. The apparatus of claim 45, wherein the second anchoring member has a diameter greater than a diameter of the strand member.

47. The apparatus of claim 45, wherein the first anchoring member and the second anchor member are deployed from their first configuration to their second configuration in response to the strand member being placed under tension.

48. An apparatus for repairing tears in soft tissue, comprising:
a cannula defining an elongate, hollow tubular body having a tissue puncturing tip at a distal end;
an implant having a lead anchoring member and a trailing anchoring member connected by a strand member, the lead anchoring member consisting of a suture material and the trailing anchoring member consisting of a suture material;
wherein the lead anchoring member is operable between a first configuration and a second configuration, wherein the first configuration enables the lead anchoring member to pass completely through an opening in the soft tissue, and a second configuration wherein the lead anchoring member cannot enter the opening in the soft tissue;
wherein the lead anchoring member is substantially linear in shape in the first configuration and is deformed into an S-shaped suture mass in the second configuration;
wherein the trailing anchoring member is operable between a first configuration and a second configuration;
wherein the trailing anchoring member is substantially linear in shape in the first configuration and is deformed into an S-shaped suture mass in the second configuration;
wherein the S-shaped suture mass comprises the leading anchoring member or trailing anchoring member in a three-two fold configuration;
wherein the implant is configured and dimensioned to be disposed within the cannula;
at least one push rod for deploying the implant from the distal lend of the cannula;
wherein the suture material of the lead anchoring member has a diameter greater than a diameter of the strand member;
wherein the suture material of the trailing anchoring member has a diameter greater than the diameter of the strand member;
wherein a diameter of the suture material of the lead anchoring member is about 0.5 millimeters;
wherein a diameter of the suture material of the trailing anchoring member is about 0.5 millimeters;
wherein a length of the lead anchoring member is about 12 millimeters;
wherein a length of the trailing anchoring member is about 12 millimeters;
wherein a length of the strand member between the lead anchoring member and the trailing anchoring member is about 30 millimeters;
wherein a diameter of the strand member is about 0.3 millimeters;
wherein the strand member comprises a suture material;
wherein the strand member defines a loop;
wherein the strand member further comprises a knot;
wherein said knot is disposed against and in contact with one of the lead an trailing anchoring members;
wherein the strand member comprises a double stranded portion that passes through the lead anchoring member and the trailing anchoring member;
wherein the cannula has an outer diameter less than 1.6 millimeters;
wherein the cannula comprises a bended portion defining an angle;
wherein the angle is about 65 degrees;
wherein the strand member comprises a first portion that passes through the lead anchoring member;
wherein the strand member further comprises a second portion that passes through the lead anchoring member;
wherein the first portion and the second portion are perpendicular to a longitudinal axis of the lead anchoring member when the lead anchoring member is in the first configuration;
wherein the strand member further comprises a third portion, wherein the third portion extends along an exterior of the lead anchoring member between the first portion and the second portion;
wherein the strand member further comprises a fourth portion that passes through the trailing anchoring member;
wherein the strand member further comprises a fifth portion that passes through the trailing anchoring member;
wherein the fourth portion and the fifth portion of the strand member are perpendicular to a longitudinal axis of the trailing anchoring member when the trailing anchoring member is in the first configuration;
wherein the strand member further comprises a sixth portion, wherein the sixth portion extends along an exterior of the trailing anchoring member between the fourth portion and the fifth portion;
wherein the lead anchoring member extends along a longitudinal axis between a proximal, terminal end face and a distal, terminal end face;
wherein the lead anchoring member includes a generally cylindrical sidewall extending between the proximal, terminal end face and the distal, terminal end face;
wherein a strand pathway extends through the lead anchoring member, the strand pathway beginning at a proximal-most opening disposed on the generally cylindrical sidewall of the lead anchoring member and ending at a distal-most opening disposed on the generally cylindrical sidewall of lead anchoring member, wherein the strand pathway of the lead anchoring member includes a first channel and a second channel, wherein the first and second channels are non-parallel when the first anchoring member is in the first configuration;

wherein the strand member extends along the strand pathway such that the strand member passes through the proximal-most opening and the distal-most opening of the strand pathway such that the strand member does not pass through either of the proximal, terminal end face or the distal, terminal end face of the lead anchoring member;

wherein the strand member comprises a double stranded portion between the proximal-most opening and the distal-most opening of the strand pathway.

\* \* \* \* \*